(12) United States Patent
Steinhardt et al.

(10) Patent No.: US 9,532,790 B2
(45) Date of Patent: Jan. 3, 2017

(54) DISPOSABLE CARTILAGE CUTTER

(71) Applicant: HEINZ KURZ GMBH MEDIZINTECHNIK, Dusslingen (DE)

(72) Inventors: Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 406 days.

(21) Appl. No.: 14/293,396

(22) Filed: Jun. 2, 2014

(65) Prior Publication Data

US 2014/0364854 A1 Dec. 11, 2014

(30) Foreign Application Priority Data

Jun. 6, 2013 (DE) .................... 20 2013 102 433 U

(51) Int. Cl.
*A61B 17/16* (2006.01)
*A61F 11/00* (2006.01)
*A61B 17/00* (2006.01)

(52) U.S. Cl.
CPC ......... *A61B 17/1635* (2013.01); *A61F 11/004* (2013.01); *A61B 2017/00787* (2013.01); *A61B 2017/00792* (2013.01); *A61B 2017/00969* (2013.01)

(58) Field of Classification Search
CPC ........................... A61B 17/1635; A61F 11/004
See application file for complete search history.

(56) References Cited

U.S. PATENT DOCUMENTS

| 2003/0216765 | A1 | 11/2003 | Efinger |
| 2010/0286693 | A1 | 11/2010 | Steinhardt et al. |
| 2012/0191093 | A1 | 7/2012 | Wong et al. |

FOREIGN PATENT DOCUMENTS

| DE | 20 2009 006 583 | 10/2010 |
| EP | 0 483 567 | 5/1992 |
| EP | 0 714 634 | 6/1996 |
| EP | 1 360 948 | 11/2003 |
| EP | 2 249 139 | 11/2010 |

*Primary Examiner* — Andrew Yang
(74) *Attorney, Agent, or Firm* — Michael J. Striker

(57) ABSTRACT

A medical cutting device for producing thin cartilage disks has a device body with a first holding device with a first working section having a first recess disposed on a top side of the device body such that the first recess is entirely or partially enclosed by a first delimiting ridge and, a connecting section that is directly, rigidly adjoined by the first working section and a cover with a counterpart section to the connecting section that is directly, rigidly adjoined by a first pressure section, which comprises a central, first pressure plate that is resiliently held in the first pressure section and, in an operating state for producing thin cartilage disks, is disposed opposite the first recess, which is entirely or partially enclosed by the first delimiting ridge.

15 Claims, 5 Drawing Sheets

DISPOSABLE CARTILAGE CUTTER

CROSS-REFERENCE TO A RELATED APPLICATION

The invention described and claimed hereinbelow is also described in German Priority Document DE 20 2013 102433.3, filed on Jun. 6, 2013. The German Priority Document, the subject matter of which is incorporated herein by reference, provides the basis for a claim of priority of invention under 35 U.S.C. 119(a)-(d).

BACKGROUND OF THE INVENTION

The invention relates to a medical cutting device for producing thin cartilage disks. The device includes a device body, a cover and a first holding device having a first section with a first recess disposed on the top side of the device body, the recess entirely or partially enclosed by a first delimiting ridge. The cutting device is made of a sterilizable material.

Frequently in medical and surgical practice, it becomes necessary to cut thin, endogeneous cartilage disks out of a larger piece of cartilage, e.g., from the auricle, the tragus, the cartilaginous portion of the upper bony rib or the nasal septum. For example, it may be necessary to examine special properties of the main body in greater detail, in particular under a microscope. In otorhinolaryngology, thin cartilage disks of this type also are required in many surgical applications, such as in the middle ear region, to cover a middle ear prosthesis, to restore the posterior wall of the auditory meatus or for the plastic repair of a defect of the tympanic membrane. Thin cartilage disks of this type are also used in many nasal surgeries in order to perform functional or aesthetic corrections of the nose.

A cutting device is described in EP 0 483 567 B1, using which thin cartilage disks having a thickness that is specifiable, within certain limits, are cut out of a larger piece of cartilage quickly reliably and with a consistent level of quality. However, to obtain different thicknesses of the cartilage disks that are created, special shims having a known thickness must be placed in the cutting device. These shims, like the cutting device itself, must be thoroughly cleaned and kept sterile and they must be handled in this manner separately before every operation, which is a time-consuming process that is susceptible to error. Considering that an average ear, nose and throat (ENT) hospital has three to four surgical suites, and that, at peak times, fifteen to twenty patients may be operated on in one day, it is possible that a cartilage cutter must be made available up to fifteen times a day. This poses a great logistical challenge in terms of supplying sterilized materials.

Moreover, handling the shims is not entirely easy. For example, due to the small size of the shims, it is not always possible to label them adequately and in an easily recognized manner, even though this is necessary in order to ensure that precisely the proper shim having the particular size that is required is available during the operation. In addition, special skills are required to insert the relatively small shims into the cutting device correctly and to fix them in position therein.

In order to ensure that thin cartilage disks having certain different thicknesses are created in a consistent level of quality, even without using the known shims, US 2010/0286693 A1 proposes that a first recess disposed in a first working section on a top side of the device body is closable via a first projection disposed on a top side of the cover, wherein the first lateral delimiting ridge comprises a first guide slot into which a cutting blade is inserted and which extends from an end face of the first section and extends parallel to the bottom surface of the first recess at a predetermined, first distance therefrom. In the device according to US 2010/0286693 A1, at least one second holding device is provided that comprises a second section having a second recess, which is disposed on the top side of the device body, the second recess being entirely or partially enclosed by a second delimiting ridge, and being closable via a second projection which is disposed on the top side of the cover. The second lateral delimiting ridge comprises a second guide slot, into which a cutting blade is inserted and which extends from an end face of the second section and extends parallel to the bottom surface of the second recess at a predetermined, second distance therefrom.

Since different distances between the particular guide slot and the corresponding bottom surface of the particular recess may be selected for different holding devices, this known cutting device makes it possible to create cartilage disks having certain different thicknesses by using the different holding devices without the need to use the shims that are indispensible in the previous prior art. In addition, the fact that the new cutting device is handled between the thumb and the index finger increases the operating surgeon's confidence in the actual cutting procedure, because all parts, due to the geometry and design thereof, are moveable relative to one another in a reliable and controlled manner.

The disadvantage of this known cutting device is that the production of the parts is highly complex. Products produced using injection-molding technology in particular have the characteristic that considerable problems can result when walls are very thin. As a result and due to the financial outlay involved, the products typically cannot be produced in a cost-effective manner.

SUMMARY OF THE INVENTION

The present invention overcomes the shortcomings of known arts, such as those mentioned above.

To that end, the present invention provides an improvement to the above-described known medical cutting device in a simple and cost-effective manner using the simplest possible technical means such that disadvantages are prevented while advantages are retained, e.g, a medical cutting device designed to ensure the cutting procedure can be performed easily, reliably and with high quality.

In an embodiment, the invention provides a medical cutting device with a device body comprising a connecting section that is directly, rigidly adjoined by a first working section, a cover with a counterpart to the connecting section, which is directly, rigidly adjoined by a first pressure section. The first pressure section has a central, first pressure plate, which is resiliently retained in the first pressure section and, in an operating state for creating thin cartilage disks, is disposed opposite the first recess, which is entirely or partially enclosed by the first delimiting ridge, and the sections are geometrically designed such that, in the operating state, the counterpart to the connecting section lies on the connecting section in a lockable manner and the first pressure section is disposed opposite the first recess of the first working section at a substantially constant first distance $d_a$ defined by the geometric shape of the connecting piece and the counterpart thereof, thereby ensuring that a first guide slot, which extends between the first working section and the first pressure section, remains free for the insertion of a cutting blade.

The pressure is regulated by resilient suspension such that a type of pressure compensation takes place in the phase of the procedure in order to ensure that the procedure is implemented smoothly. Furthermore, the resiliently suspended pressure section has the advantage that the contact pressure can be applied very easily yet accurately. The resilience enables the direct pressure to be equalized and advantageously transmitted for the cutting procedure. As a result, it is easy for the user to perform the cutting procedure in a reliable and high-quality manner.

The cutting device according to the invention makes it possible to eliminate the steps of cleaning and resterilization. This is becoming more and more important since the contamination of surgical instruments is a continuously growing problem in everyday hospital settings.

In an embodiment, the invention provides a locking device that holds a device body and a cover, in a folded-together operating state, in a fixed position relative to one another, thereby ensuring that the cartilage disk to be obtained can be reliably processed.

The locking device comprises at least one peg and at least one slot hole, into which the peg can be inserted in a locking manner.

The connecting section and the counterpart thereof are geometrically shaped such that the connecting body and the cover can be connected only in a certain, predefined direction, thereby enabling the operating surgeon to work in a virtually "blind" manner.

The connecting section of the device body comprises a receiving space on the top side, in which the recesses are formed, into which receiving space a raised area on the top side of the cover in the counterpart comprising the pressure plates can be inserted with an exact fit. Such developments of the invention are also relatively easy to manufacture.

The wall enclosing the receiving space and the wall enclosing the raised area each form a polygon having the same number of corners and the same geometry, preferably a triangle or a quadrangle, in particular a square, thereby making it easier to join the device body and cover for the folded-together operating state with an exact fit and in a manner that is possible only in one defined relative position.

The pressure plates are suspended in recesses of the pressure sections in a resilient manner, in particular, by ridge elements, which are preferably curved.

In order to better hold the cartilage pieces to be processed, the bottom surfaces of the recesses and/or the surfaces of the cover plates disposed opposite the recesses in the folded-together operating state of the device body and the cover are roughened, ribbed, or nubbly.

Preferably, the cutting device is composed of a sterilizable plastic. As a result, the cutting device may be manufactured in a much more cost-favorable manner than the typical devices, which are composed of metal. The cutting device is delivered to the operating site in a sterile package, and the cutting device is easily discarded after use. In addition, a sterile-packaged, disposable product of this type has the advantage that it is not necessary to perform time-consuming cleaning and sterilization of the cutting device before every operation, and the risk of infection is minimized. This is in contrast to the case in which sterilized materials are supplied, in which the risk of infection cannot be ruled out. Most preferably, the cutting device is manufactured using an injection-molding procedure.

In an embodiment, the cutting device includes markings formed on the working sections of the device body and/or on the corresponding sections of the cover, on which the projections are formed. The markings indicate the particular predetermined distance $d_a$, $d_b$, $d_c$ from the guide slot to the bottom surface of the corresponding recess and, therefore, the thickness of the cartilage disk that may be obtained using the particular holding device.

The markings may include numbers that indicate the particular predetermined distance from the guide slot to the corresponding recess, and therefore, the thickness of the cartilage disk that is obtainable using the particular holding device, in the metric system of measurement (e.g., in millimeters), or in the imperial system of measurement, (e.g., inches).

As an alternative or in addition, the markings may include graphical depictions such as scale marks, points, and the like to indicate the particular predetermined distance from the guide slot to the bottom surface of the corresponding recess, and, therefore, the thickness of the cartilage disk to be created, which is attained using the particular holding device.

Variants of the above-described embodiments are particularly favorable in terms of handling in which the markings are formed on the top side of the device body, in which the recesses are formed and/or on the underside of the cover, opposite the pressure plate(s).

In a further ergonomically favorable embodiment of the cutting device according to the invention, convex and/or concave gripping aids are formed on the underside of the device body, opposite the recesses and/or on the underside of the cover, opposite the cover plates, which are used for orientation purposes to apply pressure to the particular center of the projections.

Preferably, an enclosing border that extends along the edge is provided on the underside of the cover, opposite the pressure plates.

Likewise, an enclosing wall is provided on the underside of the device body that encloses one or more working spaces used for the pretreatment of a cartilage piece before cutting out the desired disk, or for the further processing of the cartilage disk that was cut out.

Round and/or oval templates that have different diameters also may be used to process the cartilage disks that are cut out.

In an embodiment of the cutting device, the templates are incorporated in a surface of the cutting device, in particular, in one of the working spaces on the underside of the device body opposite the recesses, and/or on the underside of the cover opposite the pressure plates.

In an embodiment, a measurement scale is formed in a surface of the cutting device, in particular on the underside of the device body opposite the recesses, preferably in a working space, and/or on the underside of the cover opposite the pressure plates. Using the measurement scale, the cartilage pieces to be processed and/or the cartilage disks that were cut out are easily measured. In this case as well, round or oval templates having different diameters can be incorporated for the detailed processing of the cartilage pieces.

In an embodiment, the inventive cutting device includes at least one second holding device, which has a second working section having a second recess disposed on the top side of the device body, wherein this second recess is entirely or partially enclosed by a second delimiting ridge, in that the second working section directly, rigidly adjoins the connecting section, a second pressure section directly, rigidly adjoins the counterpart to the connecting section, the second pressure section comprises a central, second pressure plate, which is resiliently held in the second pressure section, wherein this second pressure plate, in the operating state, is opposite the second recess, which is entirely or partially enclosed by the second delimiting ridge, and in that the sections are geometrically designed such that, in the operating state, the second pressure section is disposed opposite the second recess of the second working section at a substantially constant second distance $d_b$ defined by the geometric shape of the connecting piece and the counterpart thereof, thereby ensuring that a second guide slot, which extends between the second working section and the second pressure section, remains free for the insertion of a cutting blade.

In an embodiment, the inventive cutting device comprises a third holding device, which has a third working section having a third recess disposed on the top side of the device body, wherein this third recess is entirely or partially enclosed by a third delimiting ridge, wherein the third working section directly, rigidly adjoins the connecting piece, wherein a third pressure section directly, rigidly adjoins the counterpart to the connecting piece, wherein the third pressure section comprises a central, third pressure plate, which is resiliently held in the third pressure section and which, in the operating state, is disposed opposite the third recess, which is entirely or partially enclosed by the third delimiting ridge, and wherein the sections are geometrically shaped such that, in the operating state, the third pressure section is disposed opposite the third recess of the third working section at a substantially constant third distance $d_c$ defined by the geometric shape of the connecting piece and the counterpart thereof, thereby ensuring that a second guide slot, which extends between the third working section and the third pressure section, remains free for the insertion of a cutting blade, and wherein the three holding devices are preferably disposed relative to one another in the shape of a cross.

Experience has shown that it is sufficient in most cases to provide three different thicknesses of the cartilage disk to be created for a middle ear operation, in order to create an optimal match for the particular circumstances of the patient. If a finer differentiation should be carried out nevertheless, it also is possible to use a plurality of these embodiments next to one another, in which case every individual cutting device should cover a different thickness range, and a precise selection may be made on the basis of the three different thicknesses in the selected thickness range that are offered. To that end, one embodiment provides that the lateral delimiting segments are each formed as single pieces that enclose the recesses.

In an alternative class of embodiments, the lateral delimiting ridges are each formed as a plurality of individual ridges.

Preferably, the cutting blade of the inventive medical cutting device is a knife blade composed of metal, in particular a razor blade, and in which the cutting blade is retained in a knife holder that is preferably composed of plastic.

Preferably, the knife holder is designed as a single piece and comprises a slot for insertion of the cutting blade. Alternatively, the knife holder is designed as two pieces and is foldable, in order to hold the cutting blade, thereby making it easier to replace the cutting blade.

In an embodiment, the knife holder includes at least one surface, in which round and/or oval templates, which preferably have different diameters, are formed.

Preferably, a border that encloses the knife holder and extends along the edge is provided, which increases the plane-area moment and, therefore, the stability of the holder.

In an embodiment, the knife holder includes at least one and preferably a plurality of through-openings.

BRIEF DESCRIPTION OF THE DRAWINGS

Further features and advantages of the invention will become apparent from the description of exemplary embodiments that follows, with reference to the attached figures, wherein:

FIG. 4b presents a view of a top side of the cover of the cutting device depicted in FIG. 4a.

DETAILED DESCRIPTION OF THE INVENTION

Figure 1:
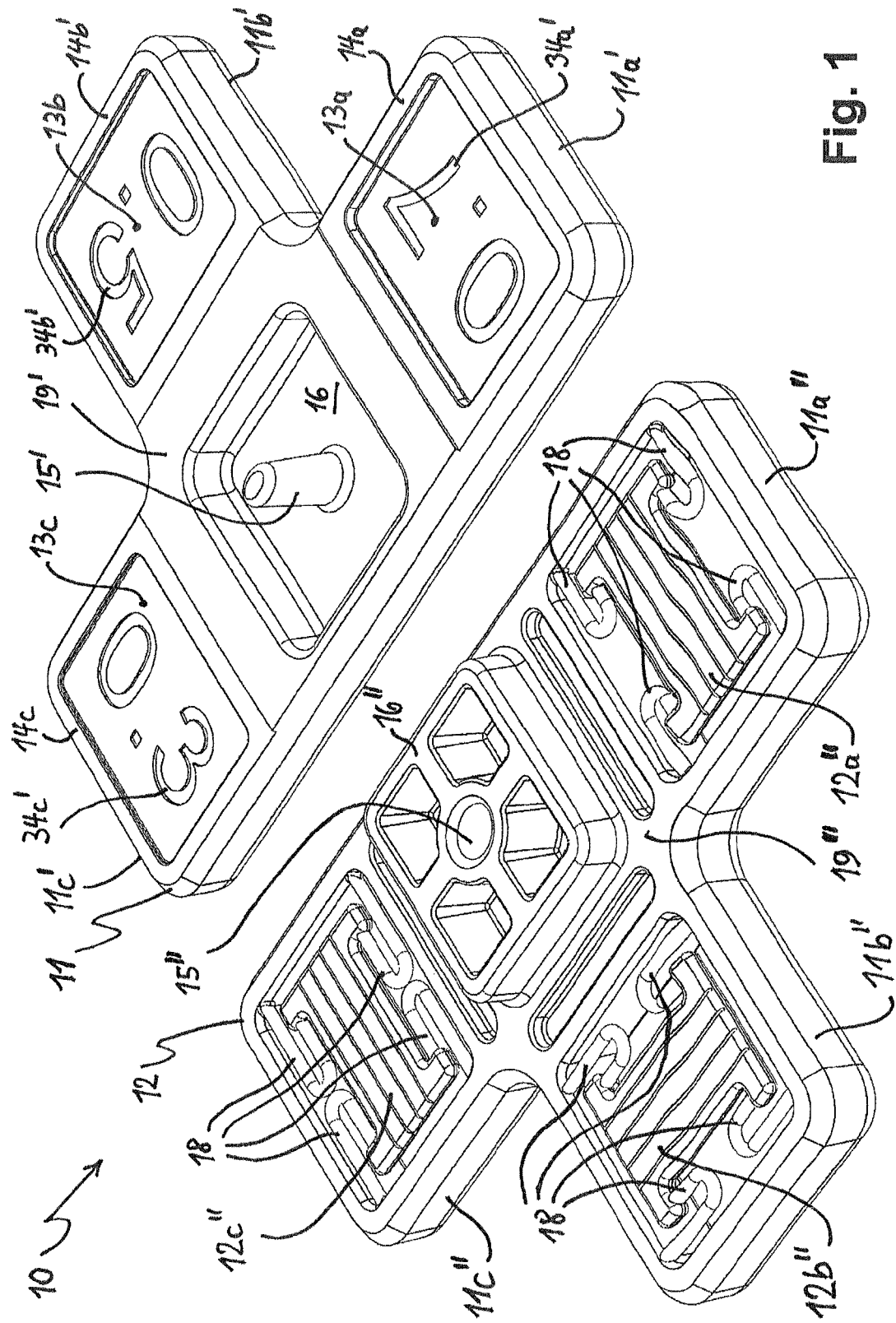
FIG. 1 is a schematic, spacial depiction a top side of a cutting device constructed according to the invention that includes three holding devices disposed in the shape of a cross.

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

The embodiments of the medical cutting device 10; 20 constructed according to the invention are designed for use in creating thin cartilage disks from a larger piece of cartilage and are made of a sterilizable material, preferably a sterilizable plastic, via an injection-molding procedure in particular. The cutting devices comprise a device body 11; 21 and a cover 12; 22, wherein a first holding device is provided, which has a first working section 11a'; 21' having a first recess 13a disposed on the top side of the device body 11; 21, wherein this first recess 13a is enclosed by a first delimiting ridge 14a in entirety or, selectively, partially by a plurality of respective individual ridges.

The cutting devices 10; 20 are characterized in that the device body 11; 21 comprises a connecting section 19'; 29', which is directly, rigidly adjoined by the first working section 11a'; 21', the cover 12; 22 comprises a counterpart 19"; 29" to the connecting section 19'; 29', which is directly, rigidly adjoined by a first pressure section 11a"; 21", the first pressure section 11a"; 21" comprises a central, first pressure plate 12a"; 22", which is resiliently held in the first pressure section 11a"; 21" and, in an operating state for producing thin cartilage disks, is disposed opposite the first recess 13a, which is entirely or partially enclosed by the first delimiting ridge 14a, and in that the sections 11a', 11a", 19', 19"; 21', 21", 29', 29" are geometrically shaped such that, in the operating state, the counterpart 19"; 29" to the connecting section 19'; 29' lies on the connecting section 19'; 29' in a lockable manner, and the first pressure section 11a"; 21" is disposed opposite the first recess 13a of the first working section 11a'; 21' at a substantially constant first distance $d_a$ defined by the geometric shape of the connecting section 19';

29'; and the counterpart 19"; 29'", thereby ensuring that a first guide slot 17a, which extends between the first working section 11a'; 21' and the first pressure section 11a"; 21", remains free for the insertion of a cutting blade 38.

Figure 2:
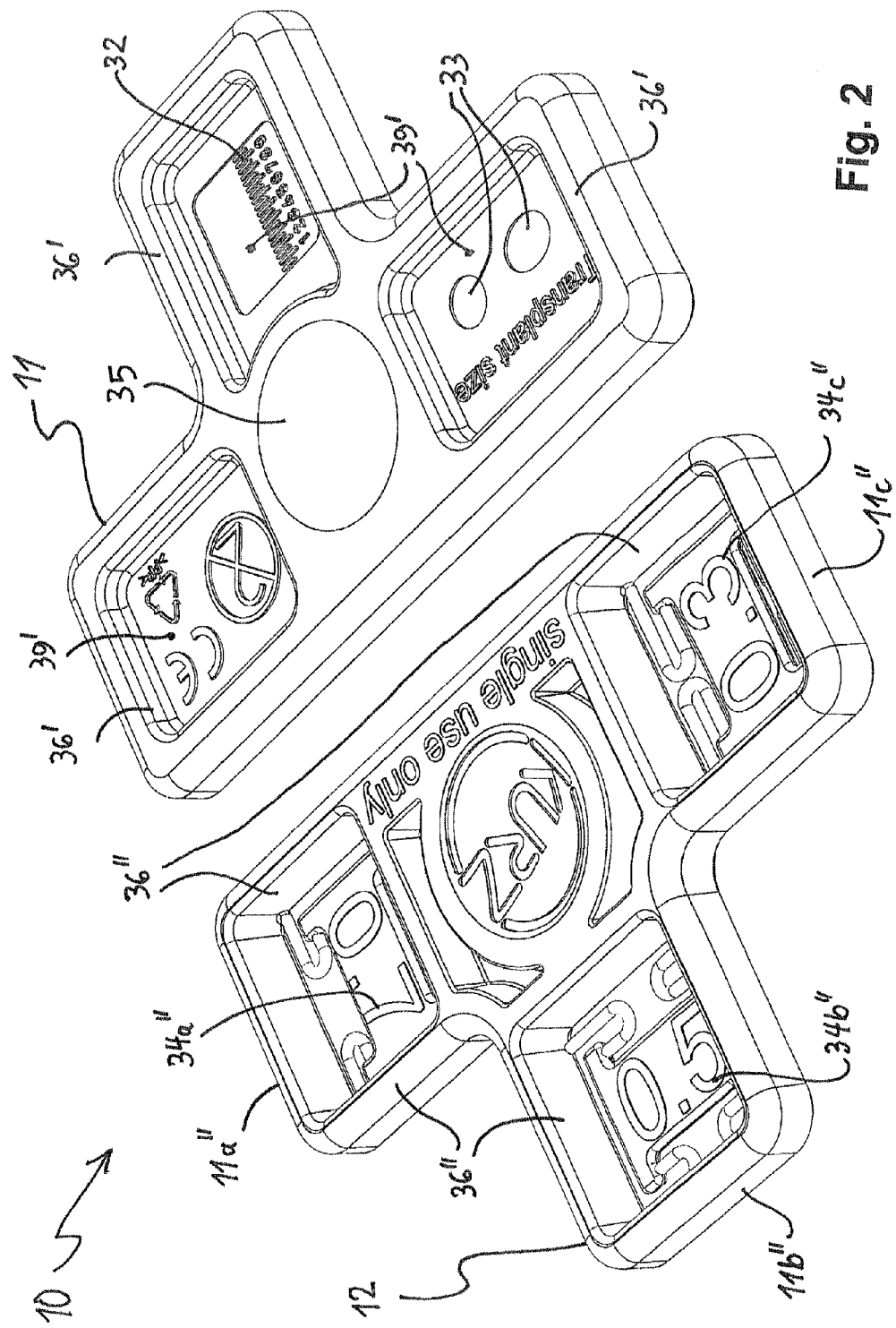
FIG. 2 presents a view of an underside of the cutting device depicted in FIG. 1.
Figure 3:
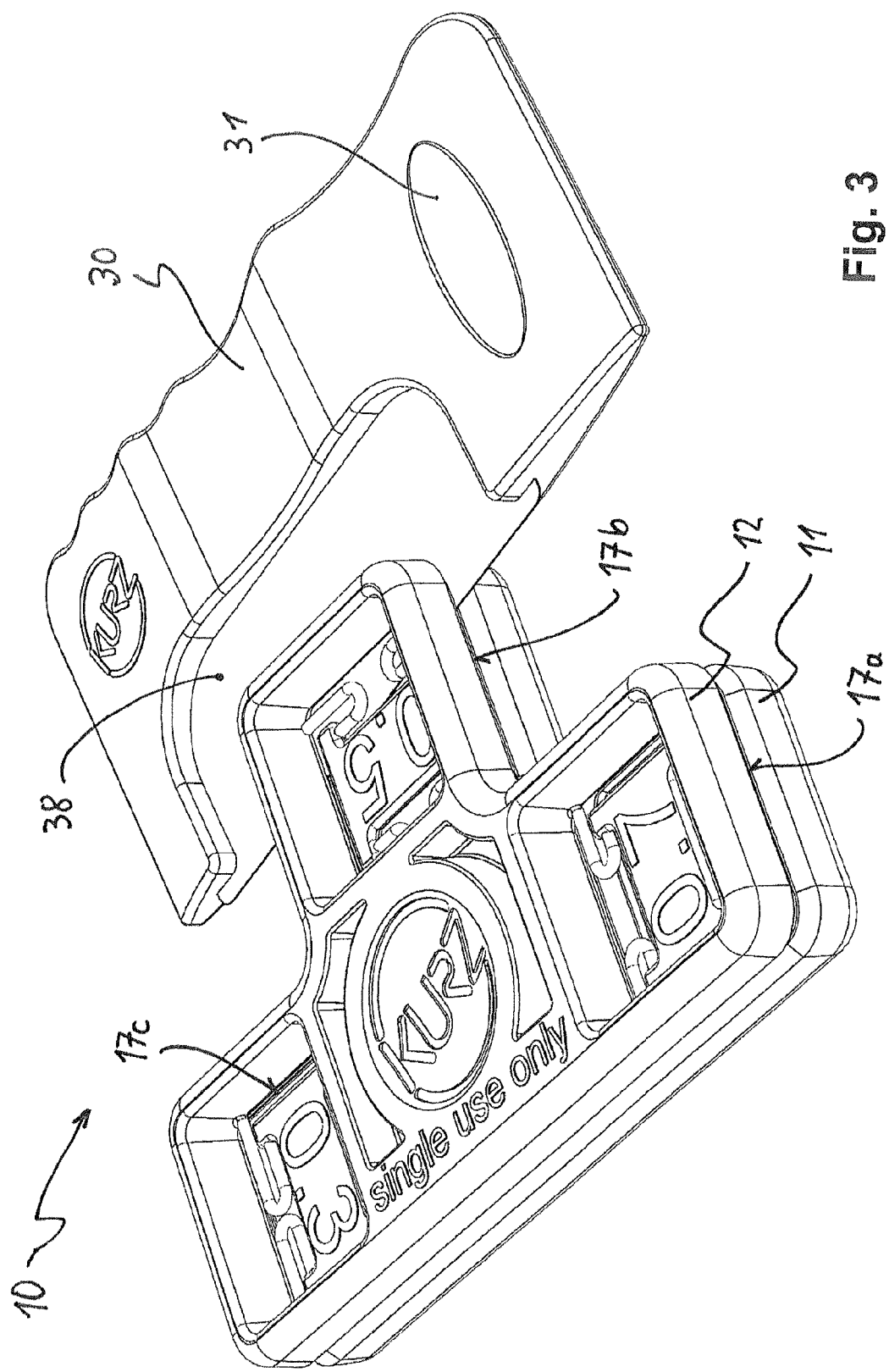
FIG. 3 presents a view of the cutting device of FIG. 1 with a cover placed on the device body and a cutting blade, including a knife holder, which has been slid into a guide slot of one of the holding devices.
Figure 4A:
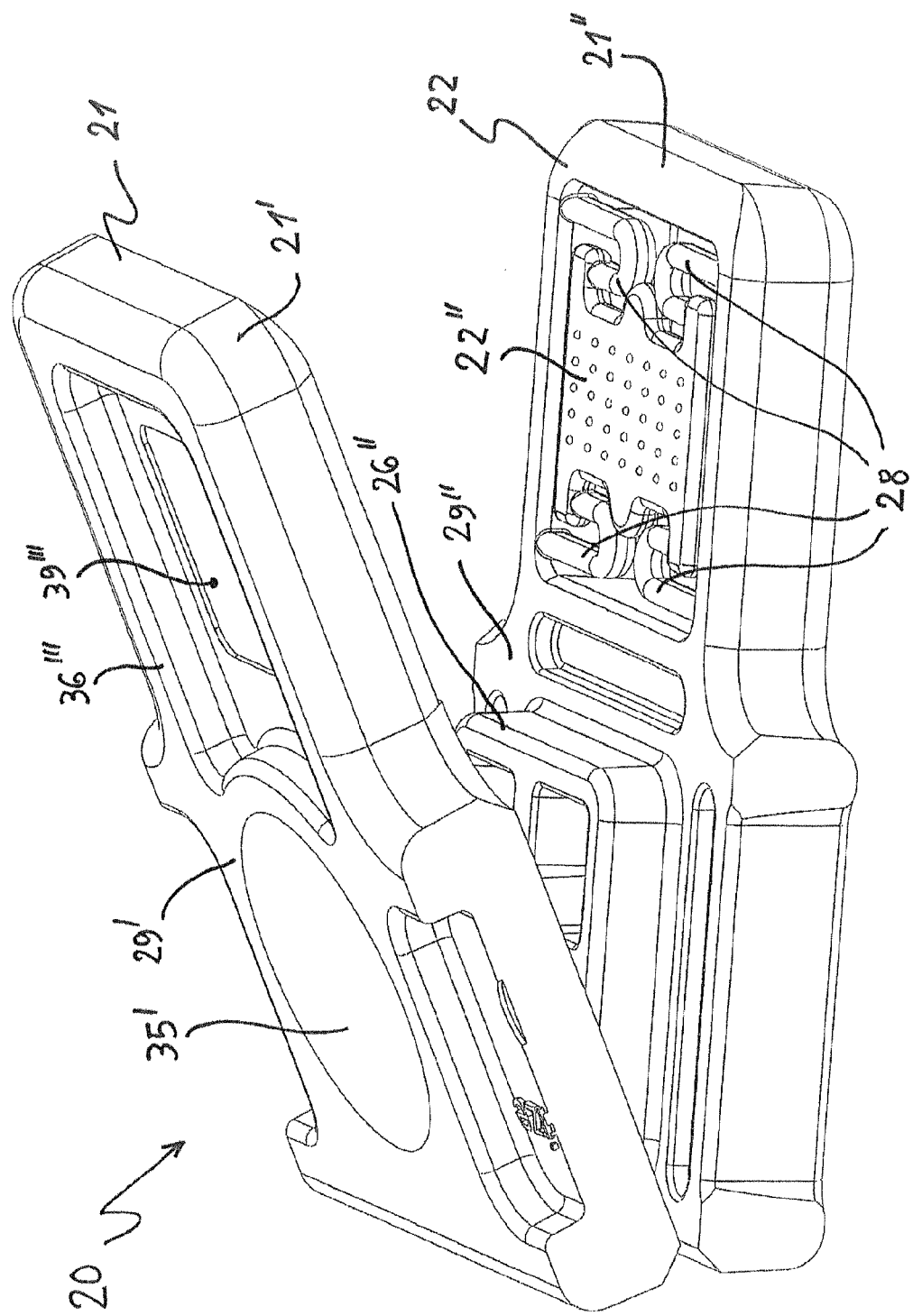
FIG. 4a presents a view of an inventive cutting device comprising a single holding device shortly before the cover is folded onto the device body.
Figure 4B:
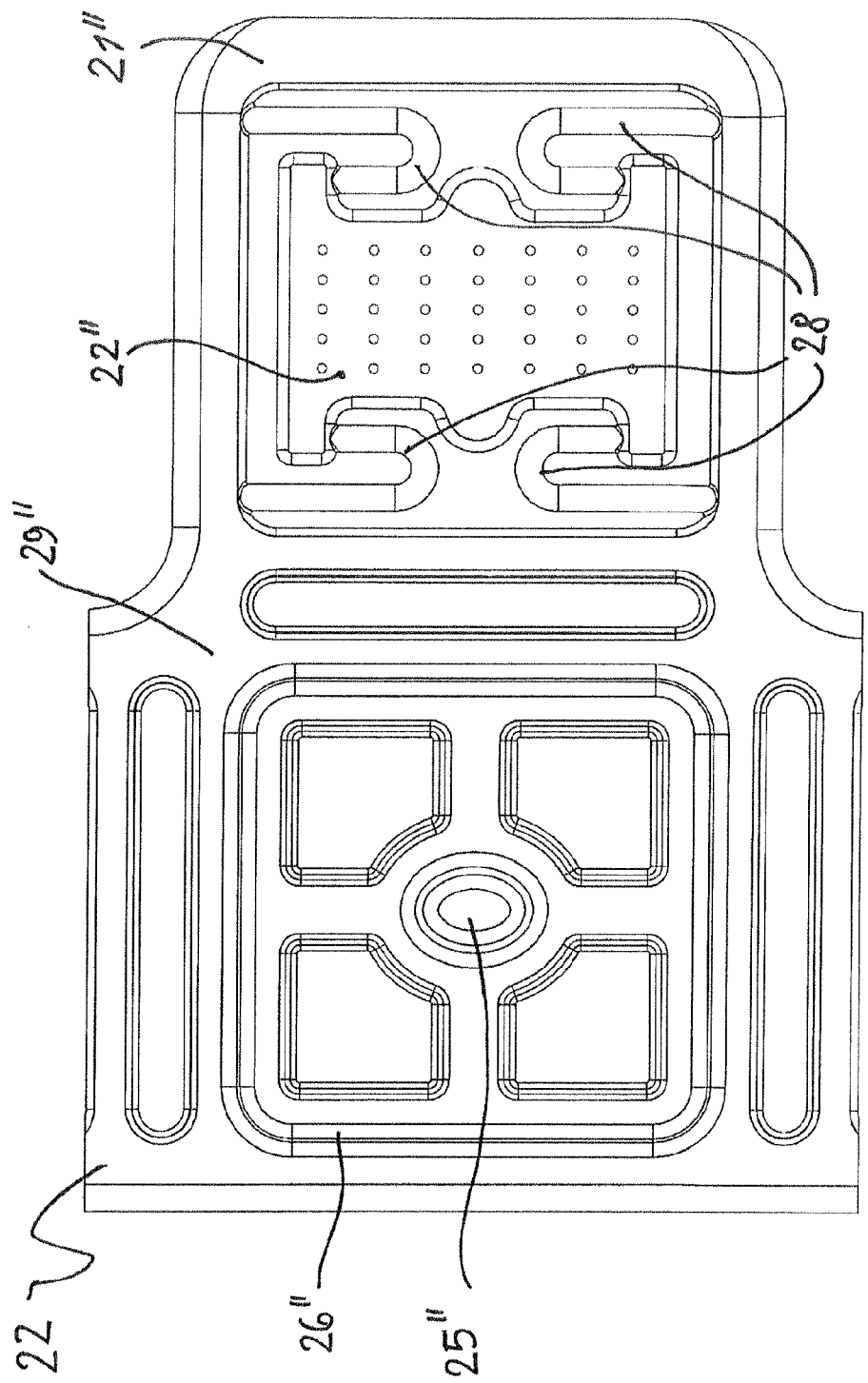

FIGS. 4a and 4b show an embodiment comprising only one holding device. In addition to this first holding device, which is used to hold the cartilage piece while a cartilage disk is cut, a second holding device can be provided and, in the exemplary embodiment depicted in FIGS. 1 to 3, a third holding device, and even further holding devices can be provided. In FIGS. 1 to 3, the three holding devices are disposed relatively close to one another, in the shape of a cross, for ergonomic reasons.

The further holding devices according to FIGS. 1 to 3 each also comprise a working section 11b', 11c' having a recess 13b, 13c, which is disposed on the top side of the device body 11 and is entirely or partially enclosed by a delimiting ridge 14b, 14c. The working sections 11b', 11c' each directly, rigidly adjoin the connecting section 19'. The pressure sections 11b", 11c" each adjoin the counterpart 19" to the connecting section 19'. These pressure sections, in turn, comprise central pressure plates 12b", 12c", which are resiliently held in the respective pressure section 11b", 11c". The sections 11b', 11b", 11c', 11c" and 19' and 19" are geometrically designed such that, in the folded-together operating state, the pressure sections 11b", 11c" are disposed opposite the recess 13b, 13c of the respectively corresponding working section 11b', 11c' at a substantially constant distance $d_b$ or $d_c$, respectively, which is defined by the geometric shape of the connecting piece 19' and the counterpart 19" thereof, thereby ensuring that a guide slot 17b, 17c, which extends between the working section 11b', 11c' and the pressure section 11b", 11c", remains free for the insertion of the cutting blade 38.

The cutting device 10; 20 according to the invention preferably comprises a locking device, which holds the device body 11; 21 and the cover 12; 22, in a folded-together operating state, in a fixed position relative to one another. As shown, this locking device comprises at least one peg 15' and at least one slot hole 15"; 25", into which the peg 15' can be inserted in a locking manner.

The connecting section 19'; 29' and the counterpart 19"; 29" thereof are geometrically shaped such that the device body 11; 21 and the cover 12; 22 are connected only in a certain, predefined direction. In the exemplary embodiments shown in the drawing, the connecting section 19'; 29' of the device body 11; 21 comprises, on the top side thereof in which the recesses 13a, 13b, 13c are formed, a receiving space 16', into which a raised area 16"; 26" on the top side of the cover 12; 22 in the counterpart 19"; 29", on which the pressure plates 12a", 12b", 12c"; 22" are disposed, can be inserted with an exact fit. The wall enclosing the receiving space 16' and the wall enclosing the raised area 16"; 26" each form a polygon having the same number of corners and the same geometry, and, in the embodiments shown in the drawing, form a square in particular. A triangular shape also is favorable for the desired definition of a certain installation direction.

The pressure plates 12a", 12b", 12c"; 22" in the embodiments of the cutting device 10; 20 are resiliently suspended in recesses of the pressure sections 11a", 11b", 11c"; 21" by curved ridge elements 18; 28.

The bottom surfaces of the recesses 13a, 13b, 13c and the surfaces of the cover plates 12a", 12b", 12c"; 22" disposed opposite the recesses 13a, 13b, 13c in a folded-together operating state of the device body 11; 21 and the cover 12; 22 are roughened, ribbed, or nubbly.

The FIGS. 1-3 embodiment shown is further characterized by the fact that markings 34a', 34b', 34c' and 34a", 34b", 34c" (in the form of numbers in this case) are formed on the working sections 11a', 11b', 11c' of the device body 11 and/or on the corresponding pressure sections 11a", 11b", 11c"; the markings indicate the respective distance $d_a$, $d_b$, $d_c$ from the guide slot 17a, 17b, 17c to the bottom surface of the corresponding recess 13a, 13b, 13c and, therefore, the thickness of the cartilage disk that may be obtained using the particular holding device by the cutting device 10, wherein this distance is given in millimeters in the present exemplary embodiment. As an alternative, the markings also may indicate the numerical values of the thickness in the imperial system of measurement, in particular in inches. As an alternative or in addition thereto, the markings also may include graphical depictions, in particular scale marks, points, or the like.

These markings 34a', 34b', 34c'; 34a", 34b", 34c" are typically formed on the top side of the device body 11, on which the recesses 13a, 13b, 13c are formed, and/or on the underside of the cover 12, opposite the pressure plates 12a", 12b", 12c".

In addition, convex and/or concave gripping aids 35; 35' and, preferably, an enclosing border 36'; 36"; 36'" that extends along the edge, are provided on the underside of the cover 12; 22, opposite the pressure plates 12a", 12b", 12c"; 22", and/or on the underside of the device body 11, opposite the recesses 13a, 13b, 13c. The walls 36'; 36'" of the device body 11; 21 enclose working spaces 39'; 39'".

Round and oval templates 33, which have different diameters and are used to further process the cartilage disks that were created, and a measurement scale 32 for measuring the cartilage disks that were processed are formed in a surface of cutting device 10, that is, in a working space 39' on the underside of the device body 11, opposite the recesses 13a, 13b, 13c.

The cutting blade 38 is typically a knife blade that is composed of metal, in particular a razor blade. In FIG. 3, for example, the cutting blade 38 is held in a single-pieced knife holder 30 that is preferably made of plastic and comprises a slot for insertion of the cutting blade 38. The knife holder 30 also may have a different design, e.g., a two-pieced design, and may be designed to be foldable in order to hold the cutting blade 38. The knife holder 30 can comprise throughopenings 31, which can be round and/or oval, for example.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A medical cutting device for producing thin cartilage disks, comprising:
    a device body with a first holding device with a first working section having a first recess disposed on a top side of the device body such that the first recess is entirely or partially enclosed by a first delimiting ridge and, a connecting section that is directly, rigidly adjoined by the first working section; and
    a cover with a counterpart section to the connecting section that is directly, rigidly adjoined by a first pressure section, which comprises a central, first pressure plate that is resiliently held in the first pressure section and, in an operating state for producing thin cartilage disks, is disposed opposite the first recess, which is entirely or partially enclosed by the first delimiting ridge, wherein first working section, connecting section, first pressure section the counterpart section to the connecting section are geometrically shaped such that, in the operating state, the counterpart section to the connecting section lies on the connecting section in a lockable manner, and the first pressure section is disposed opposite the first recess of the first working section at a substantially constant first distance $d_a$ defined by the geometric shape of the connecting section and the counterpart section to the connecting section thereof, thereby ensuring that a first guide slot, which extends between the first working section and the first pressure section, remains free for the insertion of a cutting blade.

2. The cutting device according to claim 1, wherein a locking device, holds the device body and the cover in a fixed position relative to one another in a folded-together operating state.

3. The cutting device according to claim 2, wherein the locking device comprises at least one peg and at least one slot hole into which the peg is inserted in a locking manner.

4. The cutting device according to claim 1, wherein the connecting section and the counterpart section to the connecting section are geometrically shaped such that the device body and the cover are connected in a certain, predefined direction.

5. The cutting device according to claim 4, wherein the connecting section of the device body comprises, on the top side thereof in which the recesses are formed, a receiving space, into which a raised area on the top side of the cover in the counterpart section to the connecting section, on which the pressure plates are disposed, is inserted with an exact fit.

6. The cutting device according to claim 5, wherein characterized in that a wall enclosing the receiving space and a wall enclosing the raised area each form a polygon having the same number of corners and the same geometry.

7. The cutting device according to claim 6, wherein the polygon is any of a triangle a quadrangle or a square.

8. The cutting device according to claim 5, wherein the pressure plates are resiliently suspended in recesses of the first pressure sections by curved ridge elements.

9. The cutting device according to claim 5, wherein a bottom surface of the recesses, surfaces of cover plates disposed opposite the recesses or both, in a folded-together operating state of the device body and the cover are roughened, ribbed, or nubbly.

10. The cutting device according to claim 1, wherein markings are formed on working sections of the device body, on corresponding pressure sections of the cover or both and wherein the markings indicate a respective distance $d_a$, $d_b$, $d_c$ from a guide slot to a bottom surface of the corresponding recess and, therefore, a thickness of a cartilage disk that is obtained using the holding device by the cutting device.

11. The cutting device according to any one of the preceding claims, wherein convex gripping aid, concave gripping aids or both are provided on an underside of the device body, opposite the recesses, on an underside of the cover, opposite the pressure plates or both.

12. The cutting device according to claim 11, wherein an enclosing border that extends along the edge and encloses working spaces is provided on the underside of the device body, opposite the recesses.

13. The cutting device according to claim 12, wherein a measurement scale, round or oval templates or both, having different diameters are formed in a surface of the cutting device in one of the working spaces.

14. The cutting device according to claim 1, further comprising at least one second holding device with a second working section having a second recess disposed on the top side of the device body, wherein this second recess is entirely or partially enclosed by a second delimiting ridge, wherein the second working section directly, rigidly adjoins the connecting section, a second pressure section directly, rigidly adjoins the counterpart section to the connecting section, the second pressure section comprises a central, second pressure plate, which is resiliently held in the second pressure section, wherein the second pressure plate, in the operating state, is disposed opposite the second recess, which is entirely or partially enclosed by the second delimiting ridge, and in that the second working section, the second pressure section, the connecting section and the counterpart section to the connecting section are geometrically designed such that, in an operating state, the second pressure section is disposed opposite the second recess of the second working section at a substantially constant second distance $d_b$ defined by the geometric shape of the connecting piece and the counterpart section to the connecting section thereof, thereby ensuring that a second guide slot which extends between the second working section and the second pressure section, remains free for the insertion of a cutting blade.

15. The cutting device according to claim 14, further comprising a third holding device with a third working section having a third recess disposed on the top side of the device body, wherein the third recess is entirely or partially enclosed by a third delimiting ridge, in that the third working section directly, rigidly adjoins the connecting section, a third pressure section directly, rigidly adjoins the counterpart section to the connecting section, the third pressure section comprises a central, third pressure plate, which is resiliently held in the third pressure section, wherein the third pressure plate, in the operating state, is disposed opposite the third recess, which is entirely or partially enclosed by the third delimiting ridge, and in that the third working section, the third pressure section, the connecting section and the counterpart section to the connecting section are geometrically designed such that, in the operating state, the third pressure section is disposed opposite the third recess of the third working section at a substantially constant third distance $d_c$ defined by the geometric shape of the connecting section and the counterpart section to the connecting section thereof, thereby ensuring that a third guide slot, which extends between the third working section and the third pressure section, remains free for the insertion of a cutting blade.

* * * * *